United States Patent
Castane Selga et al.

(10) Patent No.: US 9,816,965 B2
(45) Date of Patent: Nov. 14, 2017

(54) METHOD TO DETECT VIBRATION NODES BETWEEN A SENSOR AND AN ACTUATOR IN A ROTATABLE COMPONENT

(71) Applicant: General Electric Company, Schenectady, NY (US)

(72) Inventors: Rosa Castane Selga, Munich (DE); Siddharth Navinchandra Ashar, Clifton Park, NY (US); Christoph Boeld, Munich (DE); Mohamed Osama, Munich (DE); Adolfo Anta Martinez, Munich (DE)

(73) Assignee: General Electric Company, Niskayuna, NY (US)

( * ) Notice: Subject to any disclaimer, the term of this patent is extended or adjusted under 35 U.S.C. 154(b) by 365 days.

(21) Appl. No.: 14/541,953

(22) Filed: Nov. 14, 2014

(65) Prior Publication Data

US 2016/0139083 A1    May 19, 2016

(51) Int. Cl.
*G01N 29/12* (2006.01)
*F16C 32/04* (2006.01)
*G01M 13/04* (2006.01)
*G01D 5/02* (2006.01)

(52) U.S. Cl.
CPC ......... *G01N 29/12* (2013.01); *F16C 32/0444* (2013.01); *F16C 32/0453* (2013.01);
(Continued)

(58) Field of Classification Search
CPC ............... G01N 29/12; G01N 29/2475; G01N 2291/014; G01N 2291/028;
(Continued)

(56) References Cited

U.S. PATENT DOCUMENTS 5,187,434 A * 2/1993 Ando ................. G05B 19/4163
                                                        116/71
5,202,824 A    4/1993 Chen
(Continued)

FOREIGN PATENT DOCUMENTS

JP    2006195542 A    7/2006
JP    2012172756 A    9/2012
(Continued)

OTHER PUBLICATIONS

Wróblewski, Adam C., Model Identification, Updating, and Validation of an Active Magnetic Bearing High-Speed Machining Spindle for Precision Machining Operation, Dissertation for the Department of Mechanical Engineering, Cleveland State University, Aug. 2011, 139 pages.
(Continued)

*Primary Examiner* — Laura Martin
*Assistant Examiner* — Rose M Miller
(74) *Attorney, Agent, or Firm* — Pabitra K. Chakrabarti

(57) ABSTRACT

A method of detecting a vibration node between a non-collocated sensor-actuator pair of a rotatable component includes applying an excitation signal to an actuator of the sensor actuator pair. The method also includes obtaining frequency response data from the sensor-actuator pair. The method further includes analyzing the frequency response data to ascertain a resonant frequency of the rotatable component. The method includes identifying a resonance/anti-resonance peak pair in the frequency response data for the non-collocated sensor-actuator pair. Furthermore, the method includes determining whether the vibration node is located between a sensor and the actuator of the non-collocated sensor-actuator pair based on the resonance/anti-resonance peak pair.

20 Claims, 6 Drawing Sheets

(52) U.S. Cl.
CPC ........... *F16C 32/0474* (2013.01); *G01D 5/02* (2013.01); *G01M 13/045* (2013.01); *F16C 32/0487* (2013.01); *G01N 2291/014* (2013.01); *G01N 2291/028* (2013.01)

(58) Field of Classification Search
CPC .............. F16C 32/0444; F16C 32/0453; F16C 32/0474; F16C 32/0487; G01D 5/02; G01M 13/045; G01M 13/04; G01M 13/02; G01M 13/028; G01M 15/12; G01M 15/14
USPC ........................... 73/579, 660, 659, 661, 650
See application file for complete search history.

(56) References Cited

U.S. PATENT DOCUMENTS

| | | | |
|---|---|---|---|
| 5,347,190 A * | 9/1994 | Lewis | ................. F16C 32/0455 310/68 B |
| 5,486,729 A | 1/1996 | Matsushita et al. | |
| 6,770,992 B2 | 8/2004 | Yamauchi et al. | |
| 6,806,606 B2 | 10/2004 | Ohtachi et al. | |
| 6,965,181 B1 * | 11/2005 | Heshmat | ............... F16C 17/024 310/90.5 |
| 2013/0257223 A1 | 10/2013 | Kataoka | |

FOREIGN PATENT DOCUMENTS

| | | |
|---|---|---|
| JP | 5041199 B2 | 10/2012 |
| JP | 5065703 B2 | 11/2012 |

OTHER PUBLICATIONS

International Search Report and Written Opinion issued in connection with corresponding PCT Application No. PCT/US2015/054633 dated Feb. 3, 2016.

Gahler C., "Rotor dynamic Testing and Control with Active Magnetic Bearings", PhD Thesis, ETH Zurich, 196 Pages, 1998.

* cited by examiner

METHOD TO DETECT VIBRATION NODES BETWEEN A SENSOR AND AN ACTUATOR IN A ROTATABLE COMPONENT

BACKGROUND

The subject matter described herein relates generally to methods for detecting vibration nodes, and more specifically, to methods for detecting vibration nodes between a non-collocated sensor and actuator pair in a rotor-dynamic machine having an active magnetic bearing (AMB) system.

Active magnetic bearing systems are used in rotor-dynamic machines for providing non-contact operation support of a rotating piece within a mechanical system. The non-contact feature of active magnetic bearings provides decreased rotational resistance on the rotor and reduced wear on the rotating system, leading to increased efficiency and rotating system component life.

At least some known active magnetic bearing systems include at least a pair of actuators, one or more position sensors, and a controller. Furthermore, some known active magnetic bearing systems are hybrid magnetic bearing systems that include active magnetic actuators and permanent magnets. The position sensors detect a radial position of the rotor, or an actual air gap distance, relative to at least one of the actuators. The air gap distance is communicated as a signal to the controller, which compares the actual air gap distance to a preferred air gap distance for operation of the rotor. The controller then emits an excitation current relating to a change in bearing current necessary to return the rotor to the preferred air gap distance.

As the rotor is spinning, vibrations are induced into the shaft from a number of sources, including, but not limited to, rotational unbalances in the shaft and external forces, such as fluid pressure differences acting on components coupled to the rotor. As the rotational speed changes, so does the frequency of the vibrations. As the frequency changes, the rotor experiences one or more bending modes. In general, the first bending mode shape includes two nodes and one anti-node, and the second bending mode shape includes three nodes and two anti-nodes. A node is a point on the rotor that does not oscillate for a particular mode shape. An anti-node is a point on the rotor between nodes where the rotor exhibits maximum displacement.

In some known active magnetic bearing systems, a node can fall between one of the actuators and the associated position sensor. The existence of the node between the sensor and actuator pair represents a 180° shift in the displacement detected by the sensor with respect to the displacement seen by the actuator. This displacement needs to be handled by the controller. Generally, theoretical models of the rotor are not accurate enough to detect each node location over a wide frequency range. Furthermore, at least some known tests methods of known rotors require dismantling the rotor-dynamic machine to isolate the rotor. In addition, some known methods of identifying bending modes rotors can only give results for a limited number of bending modes. Thus, identifying the number of, and the precise location of, vibration nodes for various bending modes of a rotor is very difficult.

BRIEF DESCRIPTION

In one aspect, a method of detecting a vibration node between a non-collocated sensor-actuator pair of a rotatable component is provided. The non-collocated sensor-actuator pair includes at least one actuator. The method includes applying an excitation signal to the at least one actuator operatively coupled to the rotatable component. The method also includes obtaining frequency response data for the rotatable component from the non-collocated sensor-actuator pair. The method further includes analyzing the frequency response data to ascertain at least one resonant frequency of the rotatable component. In addition, the method includes identifying at least one resonance/anti-resonance peak pair in the frequency response data for the non-collocated sensor-actuator pair. Moreover, the method includes determining whether the vibration node is located between a sensor and the actuator of the non-collocated sensor-actuator pair based on the at least one resonance/anti-resonance peak pair.

In another aspect, a method of detecting a vibration node between a non-collocated sensor-actuator pair of an active magnetic bearing system is provided. The non-collocated sensor-actuator pair includes at least one electromagnetic bearing and at least one position sensor. The active magnetic bearing system includes a rotatable component and a controller. The method includes calculating at least one resonant frequency of the rotatable component based on a model of the rotatable component. The at least one calculated resonant frequency corresponds to at least one bending mode of the rotatable component. The method also includes actuating the electromagnetic bearing using a control action signal from the controller. Moreover, the method includes obtaining frequency response data for the rotatable component from the non-collocated sensor-actuator pair coupled to the rotatable component. The calculated resonant frequency is compared to the frequency response data to identify at least one resonance peak. The method includes analyzing the frequency response data to ascertain at least one resonance/anti-resonance peak pair based on the at least one resonance peak. In addition, the method includes determining whether the vibration node is located between the at least one position sensor and the at least one electromagnetic bearing of the non-collocated sensor-actuator pair for the at least one bending mode based on the at least one resonance/anti-resonance peak pair.

DRAWINGS

These and other features, aspects, and advantages of the present disclosure will become better understood when the following detailed description is read with reference to the accompanying drawings in which like characters represent like parts throughout the drawings, wherein.

Figure 1:
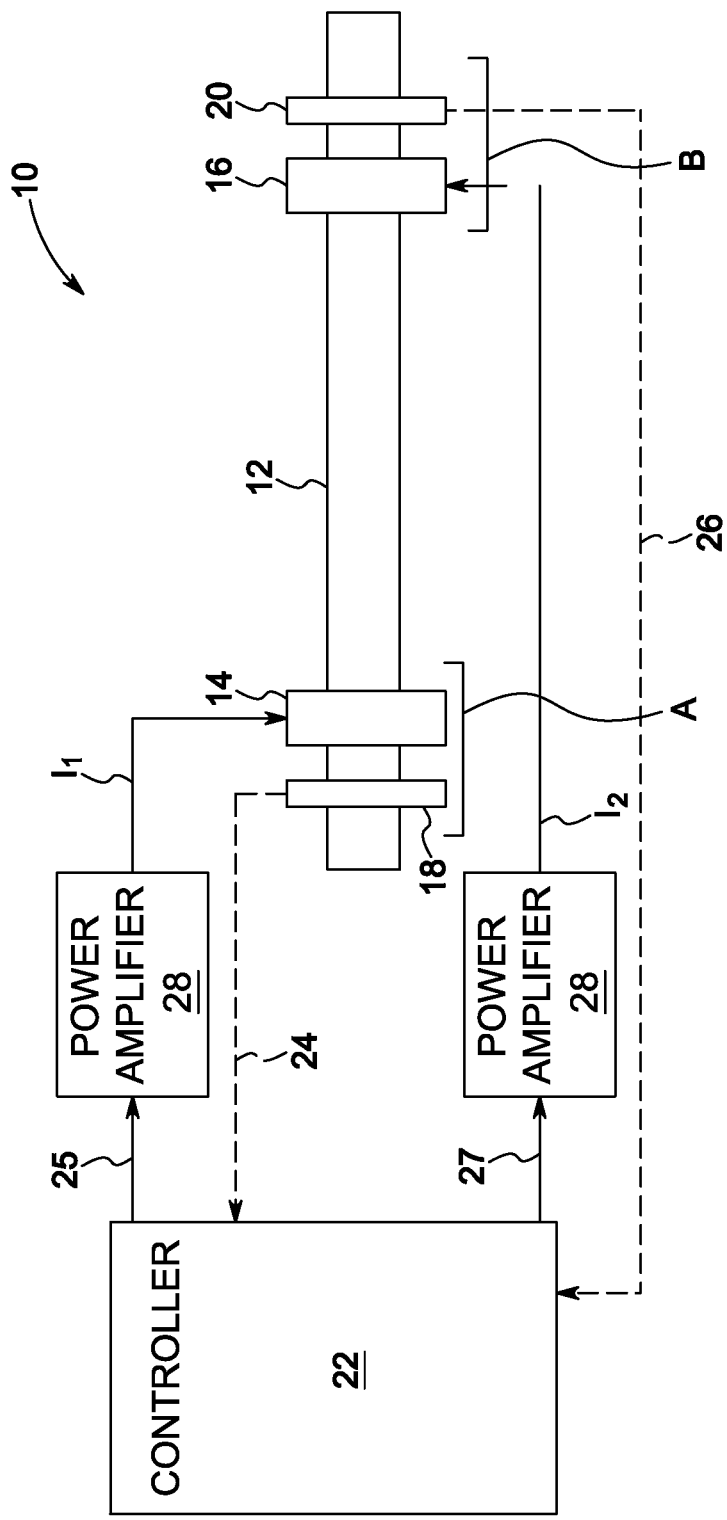
FIG. 1 is a schematic view of an exemplary active magnetic bearing (AMB) system.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings. The singular forms "a," "an," and "the" include plural references unless the context clearly dictates otherwise. "Optional" or "optionally" means that the subsequently described event or circumstance may or may not occur, and that the description includes instances where the event occurs and instances where it does not. Furthermore, references to "one embodiment" are not intended to be interpreted as excluding the existence of additional embodiments that also incorporate the recited features. Moreover, unless explicitly stated to the contrary, embodiments "including" or "having" an element or a plurality of elements having a particular property may include additional such elements not having that property.

Approximating language, as used herein throughout the specification and claims, may be applied to modify any quantitative representation that could permissibly vary without resulting in a change in the basic function to which it is related. Accordingly, a value modified by a term or terms such as "about," "approximately," and "substantially" are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

Furthermore, as used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

As used herein, the terms "processor" and "computer" and related terms, e.g., "processing device," "computing device," and "controller" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program stored in memory for execution by personal computers, workstations, clients, and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

The methods described herein facilitate the detection of vibration nodes between a non-collocated sensor-actuator pair in rotor-dynamic machines equipped with active magnetic bearings. Specifically, the methods described herein facilitate exciting a rotor with an excitation signal and detecting the frequency response using non-collocated position sensors to determine resonant frequencies of the rotor and their associated bending modes. Based on the frequency response data obtained by the position sensors, the location of vibration nodes can be determined, and in particular, vibration nodes falling between an electromagnetic actuator (or bearing) and its associated position sensor can be determined. As such, the embodiments described herein provide for reduced commissioning time for rotor-dynamic machines equipped with magnetic bearings, as they provide essential information for the controller to be adapted and adjusted to the real behavior of the rotor, enable the detection of vibration node locations in a levitated rotor without dismantling the machine to isolate the rotor, and return results for up to about 9 bending modes of the rotor, which exceeds any results obtained by traditional ping tests.

FIG. 1 is a schematic view of an exemplary active magnetic bearing system 10. In the exemplary embodiment, active magnetic bearing (AMB) system 10 may be implemented on a rotating machine (not shown) having a rotatable component, such as a rotor 12. Examples of such rotating machines include, but are not limited to, compressors, blowers, pumps, turbines, motors, and generators. AMB system 10 includes at least one active magnetic bearing. In the exemplary embodiment, AMB system 10 includes a first electromagnetic bearing or actuator 14 located proximate one end of rotor 12, and a second electromagnetic bearing or actuator 16 positioned proximate the opposite end of rotor 12. Alternatively, AMB system 10 can include any number of actuators that enable rotor 12 to function as described herein. In the exemplary embodiment, actuators 14, 16 are configured for supporting rotor 12 in a non-contact, levitating state. Further, in an alternative embodiment, each of actuators 14, 16 are of a hybrid configuration that includes a permanent magnet and electromagnet combination.

AMB system 10 includes at least one position sensor positioned adjacent each actuator 14, 16. In the exemplary embodiment, AMB system 10 includes a first position sensor 18 coupled adjacent actuator 14, and a second position sensor 20 coupled adjacent actuator 16. Actuator 14 and position sensor 18 form a non-collocated sensor-actuator pair "A," and actuator 16 and position sensor 20 form a non-collocated sensor-actuator pair "B." The term "non-collocated" as used herein refers to the actuator and its paired position sensor not being in the same axial plane, whereas "collocated" refers to the actuator and position sensor being located in the same axial plane. The term "adjacent" means near to in space or position, or next to, whether or not the two items are separated. In the exemplary embodiment, it is expected that no more than one vibration node for a particular bending mode is located between sensor-actuator pair A or sensor-actuator pair B.

In the exemplary embodiment, each position sensor 18, 20 is configured to determine an air gap distance (not shown) between rotor 12 and various positions around actuators 14, 16. In the exemplary embodiment, a total air gap distance is known, thereby enabling the air gap distance for various locations around each of actuators 14, 16 to be calculated by subtracting the measured air gap distance from the total air gap distance. In alternative embodiments, AMB system 10 includes any number of position sensors that enable AMB system 10 to function as described herein. For example, without limitation, in one embodiment, AMB system 10 includes a position sensor coupled adjacent each side of one of actuators 14, 16. Appropriate position sensors can include, without limitation, commercially-available eddy-current position sensors, inductive sensors, optical sensors, and capacitive sensors.

AMB system 10 further includes a controller 22 communicatively coupled to position sensors 18, 20. Controller 22 is configured to execute operations to control AMB system 10 based at least partially on position signals 24, 26 transmitted to controller 22 by position sensors 18, 20, respectively, and on instructions from human operators. In the exemplary embodiment, position signals 24, 26 are representative of the air gap distance between rotor 12 and a respective one of actuators 14, 16. Controller 22 includes, for example, a theoretical model of AMB system 10, and in particular, a theoretical model of rotor 12. Operations executed by controller 22 may include sensing or modeling operating parameters, modeling operational boundaries, applying operational boundary models, and applying control algorithms to control operation of AMB system 10, such as by regulating an amount of magnetic force generated by actuators 14 and 16. Controller 22 determines the axial location of a vibration node with respect to each non-collocated sensor-actuator pair A, B. The vibration node is associated with a particular bending mode of rotor 12. Based on the determined location of the vibration node, controller 22 generates control outputs, or control action signals 25, 27, to control actuators 14, 16 and the operation of AMB system 10. Commands generated by controller 22 cause actuators 14, 16 to adjust the air gap between rotor 12 and actuators 14, 16 to a desired amount.

In addition, controller 22 is coupled to power amplifiers 28, which are coupled to actuators 14, 16, respectively, for transmitting current control signals $I_1$, $I_2$ that are applied to actuators 14, 16. In the exemplary embodiment, position sensors 18, 20 are configured to transmit position signals 24, 26 that generally including an electrical voltage, indicative of the position of rotor 12 to controller 22. Normally, position sensors 18, 20 are calibrated so that the when rotor 12 is at a desired location, position sensors 18, 20 produce a null voltage. Thus, when rotor 12 is moved from the desired location, a voltage indicative of the new location is generated. For example, without limitation, when rotor 12 is moved above the desired location, a positive voltage signal is produced and when rotor 12 is moved below the desired location, a negative voltage signal is produced. However, if a vibration node of rotor 12 is located between one of actuators 14, 16 and its respective position sensor 18, 20 of non-collocated sensor-actuator pairs A, B, the position of the rotor 12 as detected by position sensors 18, 20 is 180° different than its actual position relative to actuators 14, 16.

Figure 2:
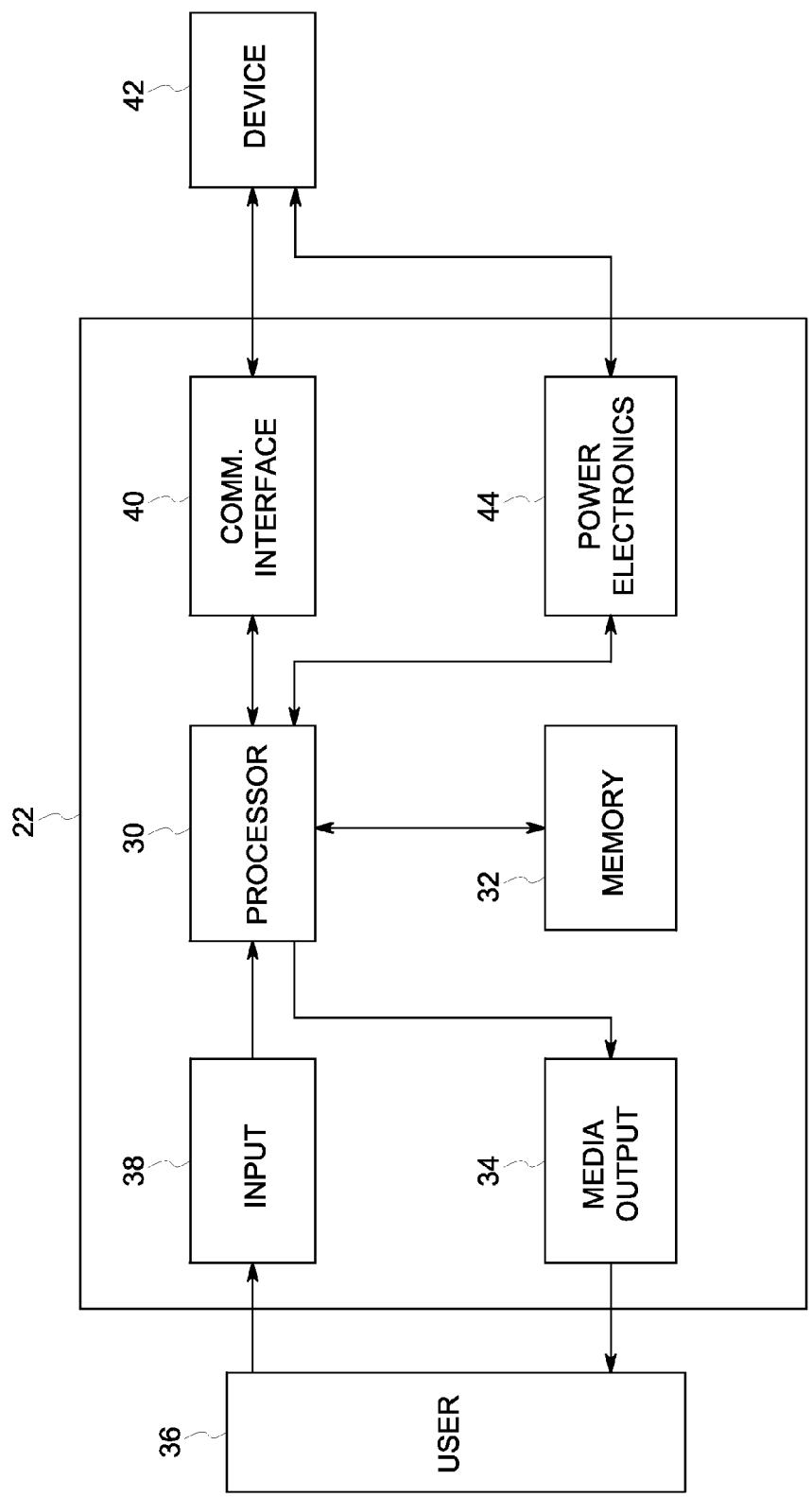
FIG. 2 is a block diagram of a controller for use with the AMB system shown in FIG. 1.

FIG. 2 is a block diagram of controller 22 for use with AMB system 10 shown in FIG. 1. Controller 22 includes a processor 30 for executing instructions. In some implementations, executable instructions are stored in a memory area 32. Processor 30 may include one or more processing units (e.g., in a multi-core configuration). Memory area 32 is any device allowing information such as executable instructions and/or other data to be stored and retrieved. Memory area 32 stores parameters for controlling the operation of AMB system 10, as described in more detail herein. Memory area 32 includes one or more computer-readable media.

In the exemplary embodiment, controller 22 includes at least one media output component 34 for presenting information to a user 36. Media output component 34 is any component capable of conveying information to user 36. In some implementations, media output component 34 includes an output adapter such as a video adapter and/or an audio adapter. An output adapter is operatively coupled to processor 30 and operatively coupleable to an output device such as a display device (e.g., a liquid crystal display (LCD), one or more light emitting diodes (LED), an organic light emitting diode (OLED) display, cathode ray tube (CRT), or "electronic ink" display) or an audio output device (e.g., a speaker or headphones). In other embodiments, controller 22 does not include media output component 34.

Controller 22 includes an input device 38 for receiving input from user 36. Input device 38 may include, for example, without limitation, one or more buttons, a keypad, a touch sensitive panel (e.g., a touch pad or a touch screen), and/or a microphone. A single component such as a touch screen may function as both an output device of media output component 34 and input device 38. Some embodiments of controller 22 do not include input device 38.

In the exemplary embodiment, controller 22 includes a communication interface 40, which is communicatively coupleable to another device 42, for example power amplifiers 28 and position sensors 18, 20. In some embodiments, communication interface 40 is configured to enable communication through a short range wireless communication protocol such as Bluetooth™ or Z-Wave™, through a wireless local area network (WLAN) implemented pursuant to an IEEE (Institute of Electrical and Electronics Engineers) 802.11 standard (i.e., WiFi), and/or through a mobile phone (i.e., cellular) network (e.g., Global System for Mobile communications (GSM), 3G, 4G) or other mobile data network (e.g., Worldwide Interoperability for Microwave Access (WIMAX)), or a wired connection (i.e., one or more conductors for transmitting electrical signals). In embodiments that communication interface 40 couples controller 22 to position sensors 18, 20, communication interface 40 may include, for example, one or more conductors for transmitting electrical signals and/or power to and/or from position sensors 18, 20. Additionally, controller 22 may also include power electronics 44, which may be coupled, for example, to processor 30 and power amplifiers 28.

In the exemplary embodiment, controller 22 receives air gap distances transmitted as position signals 24, 26 from position sensors 18, 20. Such air gap distances relate to the distance between first actuators 14 and rotor 12, and second actuator 16 and rotor 12, respectively. Controller 22 compares the air gap distances to a predetermined value range for air gap distance. In the exemplary embodiment, controller 22 generates control action signals 25, 27 based on the comparison. The control action represents a force necessary to position rotor 12 back to the predetermined value range. Upon determining the control action, controller 22 transmits control action signals 25, 27 to amplifiers 28. In the exemplary embodiment, control action signals 25, 27 correspond to current requirements for actuators 14, 16.

In the exemplary embodiment, current control signals $I_1$ and $I_2$ pass through power amplifiers 28 to provide an appropriate amount of current to actuators 14, 16, which provide an attractive force to correct the position of rotor 12 along each actuator 14, 16. In some embodiments, power amplifiers 28 are voltage switches that are turned on and off at a high frequency, as commanded by control action signals 25, 27 from controller 22. In such embodiments, control action signals 25, 27 are pulse width modulation (PWM) signals.

In the exemplary embodiment, AMB system 10 operates as a closed-loop system. AMB system 10 has a sample rate in the range between about 2,000 cycles per second to about 100,000 cycles per second, which may also be referred to as having a sample rate frequency in the range between about 2 kilohertz (kHz) and 100 kHz.

Figure 3:
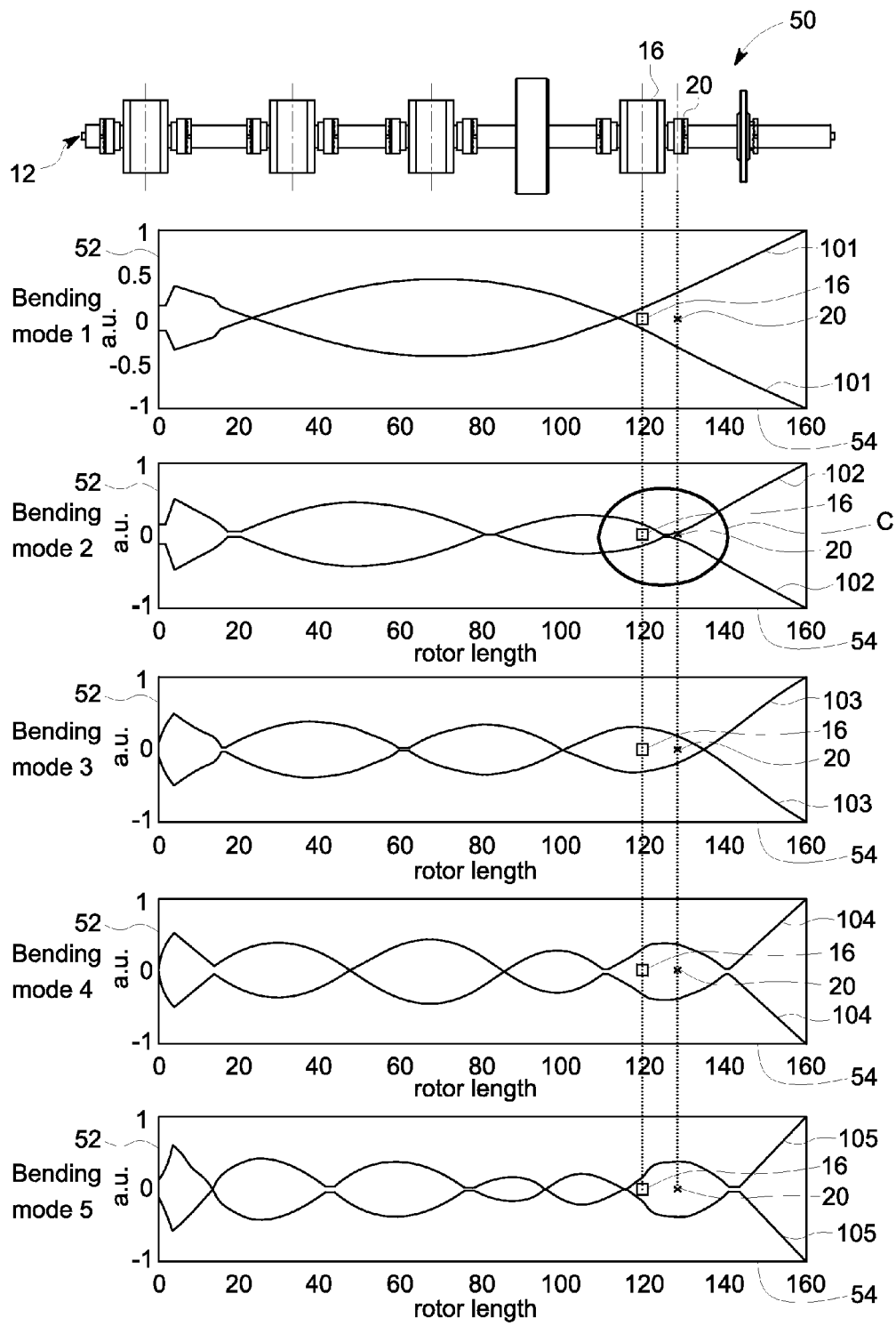
FIG. 3 is a series of schematic graphs showing theoretical bending shapes for a plurality of bending modes of a rotor of the AMB system of FIG. 1.

FIG. 3 is a series of schematic graphs 50 showing theoretical bending shapes for a plurality of bending modes of rotor 12. In the exemplary embodiment, rotor 12 has the geometry of a flexible beam, i.e., rotor 12 exhibits flexural vibrations resulting in various bending mode shapes at specific frequencies. Y-axis 52 represents the magnitude of deflection of rotor 12 in increments of 0.5 arbitrary units (a.u.) extending from −1 to 1, where the deflection amount is scaled to a maximum deflection of 1, which is equivalent to the maximum deflection of rotor 12. X-axis 54 represents the length of rotor 12 in increments of 20 arbitrary units (a.u.) extending from 0 to 160. As shown in FIG. 3, the shape of bending mode 1 is represented by curve 101, bending mode two is represented by curve 102, bending mode 3 is represented by curve 103, bending mode 4 is represented by curve 104, and bending mode 5 is represented by curve 105. In the exemplary embodiment, each bending mode shape curve 101, 102, 103, 104, and 105 is generated based on a theoretical or mathematical model of rotor 12. For simplicity, rotor 12 is shown with actuator 16 represented in each graph as a square shape along the "0" line of the Y-axis and position sensor 20 represented in each graph as an "X" shape along the "0" line of the Y-axis. A vibration node, or null, of rotor 12 occurs at each point of the graph that shape curves 101, 102, 103, 104, and 105 intersect with each other along the "0" line of the Y-axis. In the exemplary embodiment, the theoretical model indicates that there is a node between sensor 20 and actuator 16 at the second bending mode, as generally shown at reference character "C."

Figure 4:
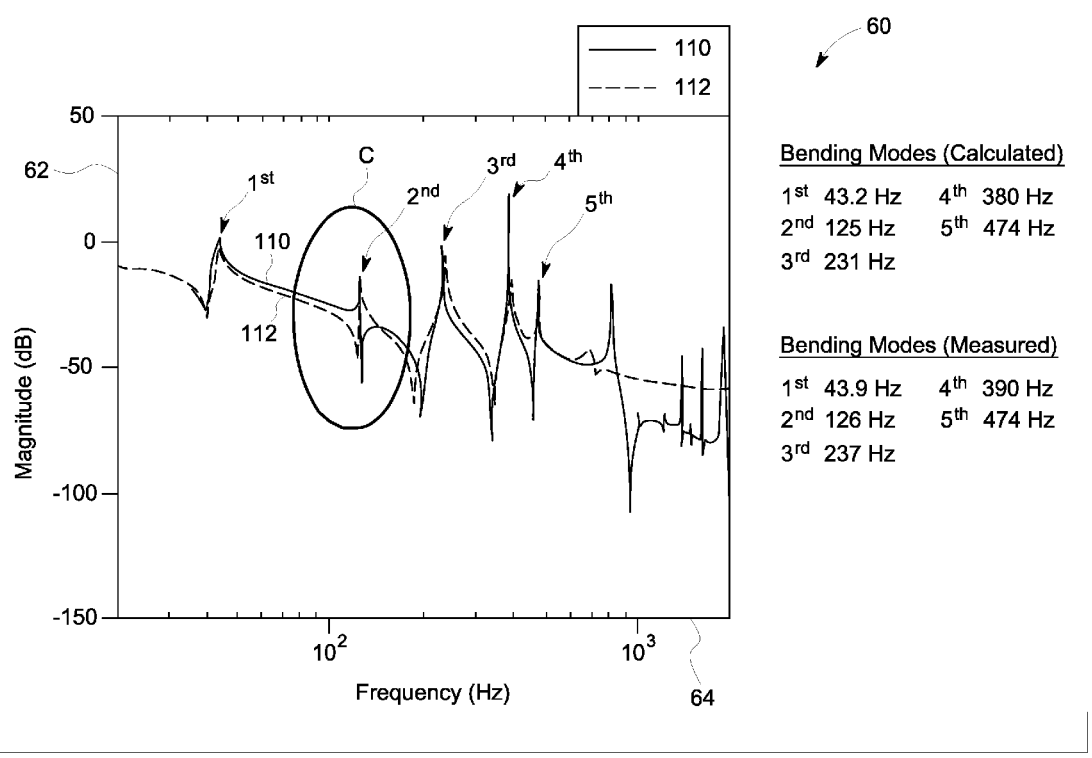
FIG. 4 is a schematic plot displaying the magnitude of the frequency response of the rotor, shown in FIG. 3, at a position sensor over a wide range of frequencies.

FIG. 4 is a schematic plot 60 displaying the magnitude of the frequency response of rotor 12, shown in FIG. 3, at position sensor 20 over a wide range of frequencies. Y-axis 62 represents the magnitude of the frequency response of rotor 12 in increments of 50 decibels (dB) extending from −150 to 50. X-axis 64 represents frequency in Hertz (Hz) plotted on a logarithmic scale, extending from about 20 to about 2000. Curve 110 represents the theoretical frequency response of rotor 12 at position sensor 20. Curve 112 represents the actual frequency response of rotor 12 at position sensor 20 as determined by position sensor 20 during system identification. Further, as shown in FIG. 4, the theoretical resonant frequencies for bending modes 1 through 5 for rotor 12, as calculated, are shown. In the exemplary embodiment, the system natural frequencies, i.e., resonant peaks or poles are defined by the peaks of curve 110, and they generally correspond to the calculated natural resonant frequencies of rotor 12. Each resonant frequency peak associated with the respective bending modes 1 through 5 are labeled on plot 60, generally indicated as $1^{st}$, $2^{nd}$, $3^{rd}$, $4^{th}$ and $5^{th}$. The anti-resonant peaks, or zeros, are shown as the negative peaks of curves 110, 112, and are generally adjacent a respective resonant peak. The detected resonant frequencies for each bending mode for rotor 12, as measured by position sensor 20 during system identification, are shown and generally correspond to the peaks of curve 112. Area "C" corresponds to area "C" shown in FIG. 3 and is described in detail herein.

Figure 5:
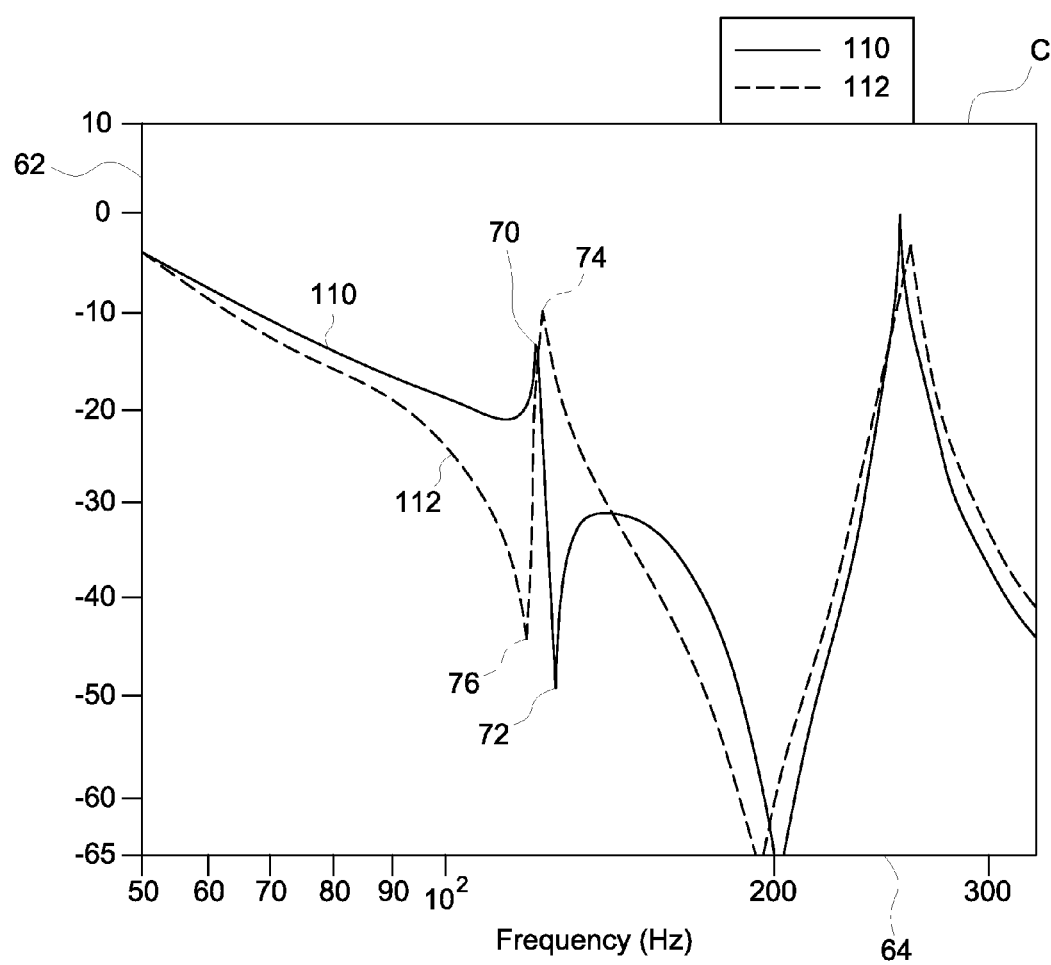
FIG. 5 is an enlarged view of FIG. 4 identified by area C, showing frequency response curves of the rotor shown in FIG. 3.

FIG. 5 is an enlarged view of FIG. 4 identified by area C, showing frequency response curves 110, 112. In the exemplary embodiment, a vibration node falls between a sensor-actuator pair, e.g., sensor-actuator pair B (shown in FIG. 1), when an anti-resonance peak follows the corresponding resonance peak. This is because collocated sensor-actuator pair systems exhibit alternating resonance peaks (poles) and anti-resonant peaks (zeros). This is referred to as pole-zero interlacing. Non-collocated sensor-actuator pair systems, however, do not have the property of pole-zero interlacing due to pole-zero flipping. Pole-zero flipping occurs in non-collocated sensor-actuator pair systems because when a vibration node exists between the sensor-actuator pair, the sensor will detect a resonant peak at a lower frequency than an anti-resonance peak. In collocated sensor-actuator pair systems, anti-resonance occurs between consecutive resonant frequencies. As shown in FIG. 5, curve 110 has a resonant peak 70 preceding an anti-resonant peak 72, thus the theoretical model of rotor 12 predicts that a vibration node exists between actuator 16 and position sensor 20, or sensor-actuator pair B. This is due to the shape of bending mode 2 shown in FIG. 3. The vibration node of the second bending mode lies between actuator 16 and position sensor 20. Thus, as the location of position sensor 20 moves away from actuator 16, the anti-resonance peak passes by the resonant peak and moves to a higher frequency, and thus the property of pole-zero interlacing is lost. In the exemplary embodiment, curve 112, which represents the actual measured response of rotor 12, has a resonant peak 74 that follows an anti-resonant peak 76, thus indicating that no node exists between sensor-actuator pair B.

Figure 6:
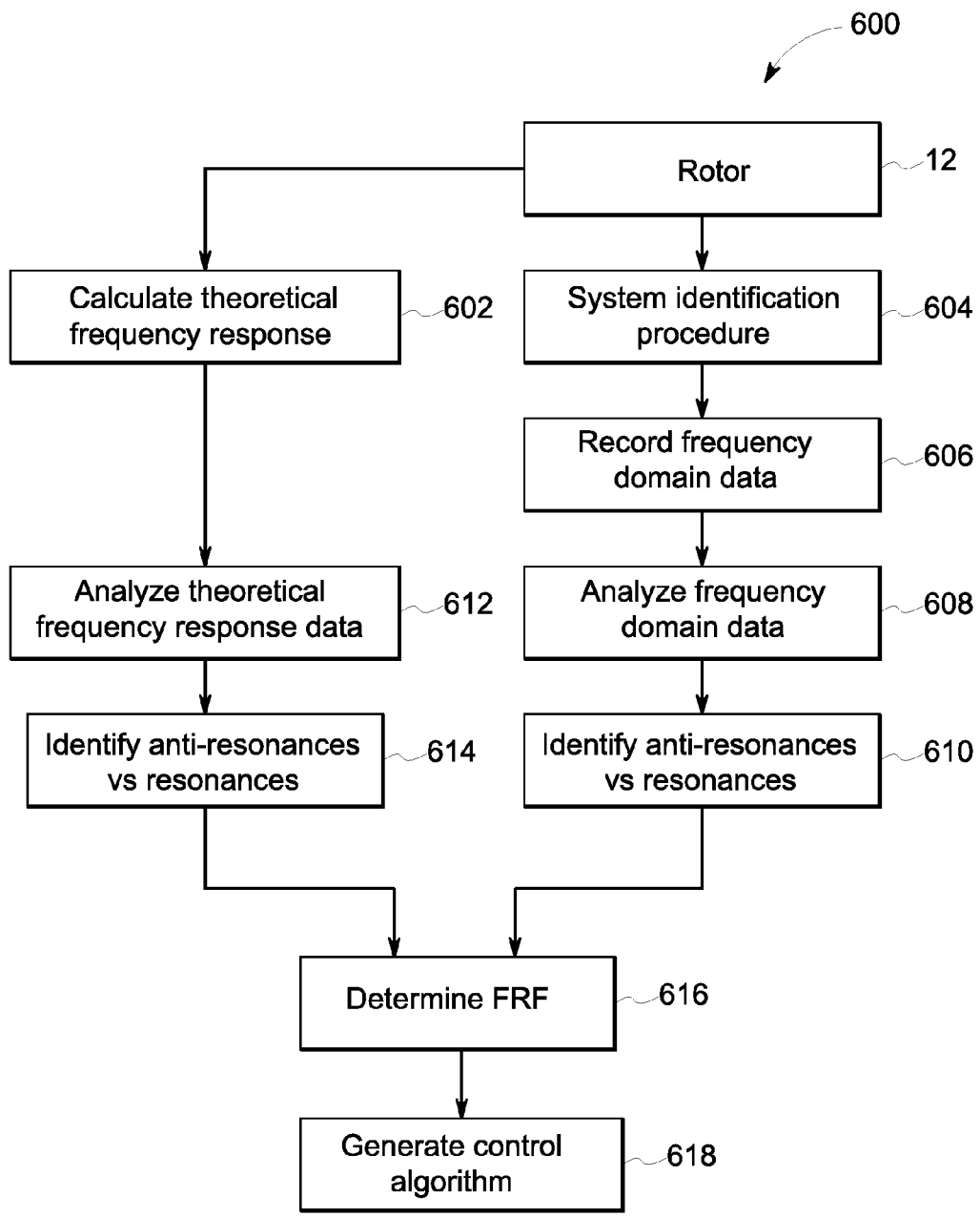
FIG. 6 is a block diagram of an exemplary method for detecting vibration nodes between a sensor-actuator pair of the AMB system shown in FIG. 1.

FIG. 6 is a block diagram of an exemplary method 600 for detecting vibration nodes between a sensor-actuator pair of AMB system 10 (shown in FIG. 1). In the exemplary embodiment, AMB system 10 includes rotor 12 (shown in FIG. 1) positioned between opposing first and second actuators 14, 16 (shown in FIG. 1) and controller 22 (shown in FIG. 1). Also, in the exemplary embodiment, method 600 includes two parallel processes. The parallel processes are implemented simultaneously or separately, and in real-time during operation of AMB system 10 or off-line. In the exemplary embodiment, rotor 12 is levitated using actuator 14, 16. The theoretical and actual frequency response of rotor 12 is determined by system identification procedures, as described further below. The theoretical frequency response data of rotor 12 is calculated 602 using a theoretical model of AMB system 10, and in particular, rotor 12. Based on the theoretical frequency response of rotor 12, a base control algorithm is designed and programmed into controller 22 for stabilized control of AMB system 10. However, due to unknown variables in AMB system 10, for example, without limitation, fabrication variations in rotor 12, vibration nodes may or may not fall between a sensor-actuator pair, such as sensor-actuator pair B. Therefore, the actual frequency response of rotor 12 is needed to facilitate proper control of AMB system 10.

In the exemplary embodiment, the actual frequency response of rotor 12 is obtained by applying 604 a system identification procedure in which an excitation signal— added to the control action signals 25, 27—is transmitted to actuators 14, 16 simultaneously with the levitation of rotor 12 by actuators 14, 16. The excitation signal induces a vibratory response, or frequency response behavior in rotor 12, such that the response is detected and an amount of displacement is measured by position sensors 18, 20. Alternatively, a frequency response behavior is induced in rotor 12 by any manner that enables detection of vibration nodes as described herein, for example, without limitation, by physically impacting rotor 12. In the exemplary embodiment, the measured responses, or frequency response data, are recorded 606 and is referred to as non-parametric data. In the exemplary embodiment, the excitation signal is a signal that induces a response from rotor 12 across a wide range of frequencies. In one embodiment, the excitation signal is configured to induce a response in rotor 12 that covers a range of frequencies associated with the first 10 bending modes of rotor 12. Alternatively, the excitation signal is configured to induce a response in rotor 12 over any predetermined frequency range based on the theoretical frequency responses calculated for rotor 12.

In the exemplary embodiment, the non-parametric data is collected and stored in memory area 32 of controller 22. Alternatively, the data is collected and stored manually or in any computer system that enables AMB system 10 to undergo the system identification procedure as described herein. In the exemplary embodiment, the method includes retrieving the non-parametric data from memory area 32 and analyzing 608 the non-parametric data to ascertain the resonant frequencies and bending modes of rotor 12. Further, the method includes identifying 610 resonance/anti-resonance peak pairs for each sensor-actuator pair A, B, corresponding to each of the bending modes of AMB system 10. Further, to identify the resonance/anti-resonance peak pairs corresponding to each of the bending modes, the theoretical frequency response data of rotor 12 is analyzed 612 to identify 614 theoretical resonance/anti-resonance peak pairs corresponding to each of the bending modes.

In the exemplary embodiment, the resonance/anti-resonance peak pairs associated with the non-parametric data is analyzed to determine 615 if a vibration node lies between a sensor-actuator pair. A vibration node falls between the sensor-actuator pair when the anti-resonance peak is at a higher frequency than the corresponding resonance peak. However, if the anti-resonance peak is at a lower frequency than the corresponding resonance peak, there is no node between the sensor-actuator pair. The non-parametric data is used to determine 616 a frequency response function, or transfer function, of rotor 12, thereby enabling generation of a parametric model of rotor 12. The parametric model of rotor 12 is used to facilitate generating 618 a control algorithm for the identified AMB system 10. The identified control algorithm is implemented in controller 22 to facilitate accurate control of rotor 12.

The embodiments described herein enable the detection of vibration nodes between a non-collocated sensor-actuator pair in rotor-dynamic machines equipped with active magnetic bearings. Additionally, the detection of vibration nodes between a non-collocated sensor-actuator pair enables manual or automatic adjustment of the control algorithm to account for the actual location of the vibration nodes. Furthermore, the detection method is based on actual real-world rotor behavior, which improves upon results obtained by theoretical models subjected to uncertainty. The detection method can be performed in a levitated rotor without the need to dismantle the rotor-dynamic machine to isolate the rotor. In addition, the detection method can give results up to about 9 bending modes of the rotor, which exceeds results obtained by traditional ping tests methods.

An exemplary technical effect of the methods, systems, and apparatus described herein includes at least one of: (a) detecting whether a vibration node is located between a sensor-actuator pair of a rotor; (b) generating a control algorithm to account for the actual location of the vibration node; (c) achieving higher control performance in operating a rotor in a magnetic bearing system; and (d) enabling faster commissioning time by eliminating the need to perform traditional ping tests and dismantling of the rotor-dynamic machine to isolate the rotor.

Exemplary embodiments of methods for detecting vibration node locations in a rotor of a rotor-dynamic machine are described above in detail. The system and methods described herein are not limited to the specific embodiments described, but rather, components of systems and/or steps of the methods may be utilized independently and separately from other components and/or steps described herein. For example, the methods may also be used in combination with other magnetic bearing systems and detection methods, and are not limited to practice with only the systems and methods, as is described herein. Rather, the exemplary embodiments can be implemented and utilized in connection with many rotor-dynamic machine system applications.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of detecting a vibration node between a non-collocated sensor-actuator pair of a rotatable component, the non-collocated sensor-actuator pair including a sensor and at least one electromagnetic bearing, the at least one electromagnetic bearing supporting the rotatable component for rotation therein, said method comprising:

actuating the electromagnetic bearing using a control action signal from a controller;

adding an excitation signal to the control action signal;

applying the excitation signal to the at least one electromagnetic bearing operatively coupled to the rotatable component;

obtaining frequency response data for the rotatable component from the non-collocated sensor-actuator pair;

analyzing the frequency response data to ascertain at least one resonant frequency of the rotatable component;

identifying at least one resonance/anti-resonance peak pair in the frequency response data for the non-collocated sensor-actuator pair; and determining whether the vibration node is located between the sensor and the at least one electromagnetic bearing of the non-collocated sensor-actuator pair based on the at least one resonance/anti-resonance peak pair.

2. The method in accordance with claim 1 further comprising actuating the at least one electromagnetic bearing using a control action signal from a controller to levitate the rotatable component.

3. The method in accordance with claim 1 further comprising measuring an amount of displacement of the rotatable component with the sensor located adjacent the at least one electromagnetic bearing, wherein the sensor and the at least one electromagnetic bearing define the non-collocated sensor-actuator pair.

4. The method in accordance with claim 1 further comprising storing the frequency response data in a memory area of a controller.

5. The method in accordance with claim 1, wherein the at least one resonance/anti-resonance peak pair includes a resonance peak and an anti-resonance peak, and wherein the resonance peak corresponds to the at least one resonant frequency of the rotatable component.

6. The method in accordance with claim 5, wherein determining whether the vibration node is located between the sensor and the at least one electromagnetic bearing of the non-collocated sensor-actuator pair comprises determining that the vibration node is located between the sensor and the at least one electromagnetic bearing when the anti-resonance peak follows the corresponding resonance peak of the at least one resonance/anti-resonance peak pair.

7. The method in accordance with claim 1 further comprising determining a transfer function of the rotatable component based on the frequency response data of the rotatable component.

8. The method in accordance with claim 7 further comprising generating a parametric model of the rotatable component based on the transfer function.

9. The method in accordance with claim 8 further comprising modifying a control algorithm of a controller operatively coupled to the at least one electromagnetic bearing based on the transfer function of the rotatable component.

10. A method of detecting a vibration node between a non-collocated sensor-actuator pair of an active magnetic bearing system, the non-collocated sensor-actuator pair including at least one electromagnetic bearing and at least one position sensor, the active magnetic bearing system including a rotatable component and a controller, said method comprising:

calculating at least one resonant frequency of the rotatable component based on a model of the rotatable component, the at least one calculated resonant frequency corresponding to at least one bending mode of the rotatable component;

determining a control algorithm for stabilized control of the active magnetic bearing system based on the at least one calculated resonant frequency;

generating a control action signal based on the control algorithm;

actuating the electromagnetic bearing using the control action signal from the controller;

inducing a frequency response in the rotatable component using the control action signal;

obtaining frequency response data for the rotatable component from the non-collocated sensor-actuator pair coupled to the rotatable component;

comparing the at least one calculated resonant frequency to the frequency response data to identify at least one resonance peak;

analyzing the frequency response data to ascertain at least one resonance/anti-resonance peak pair based on the at least one resonance peak; and determining whether the vibration node is located between the at least one position sensor and the at least one electromagnetic bearing of the non-collocated sensor-actuator pair for the at least one bending mode based on the at least one resonance/anti-resonance peak pair.

11. The method in accordance with claim 10 further comprising physically impacting the rotatable component to induce vibrations into the rotatable component.

12. The method in accordance with claim 10 further comprising applying an excitation signal to the electromagnetic bearing using the controller, wherein the excitation signal is added to the control action signal, and wherein the excitation signal is configured to induce vibrations into the rotatable component.

13. The method in accordance with claim 10 wherein obtaining frequency response data for the rotatable component comprises measuring an amount of displacement of the rotatable component with the least one position sensor.

14. The method in accordance with claim 10 further comprising storing the frequency response data in a memory area of the controller.

15. The method in accordance with claim 10, wherein the at least one resonance peak substantially corresponds to the at least one calculated resonant frequency of the rotatable component.

16. The method in accordance with claim 10, wherein the at least one resonance/anti-resonance peak pair includes the at least one resonance peak and an associated anti-resonance peak.

17. The method in accordance with claim 16, wherein determining whether the vibration node is located between the at least one position sensor and the at least one electromagnetic bearing of the non-collocated sensor-actuator pair comprises determining that the vibration node is located between the at least one position sensor and the at least one electromagnetic bearing when the anti-resonance peak follows the associated resonance peak of the at least one resonance/anti-resonance peak pair.

18. The method in accordance with claim 10 further comprising determining a transfer function of the rotatable component based on the frequency response data.

19. The method in accordance with claim 18 further comprising generating a parametric model of the rotatable component based on the transfer function.

20. The method in accordance with claim 19 further comprising modifying the control action signal of the controller based on the transfer function of the rotatable component.

* * * * *